United States Patent [19]
Nakamura et al.

[11] Patent Number: 6,060,480
[45] Date of Patent: May 9, 2000

[54] PREVENTIVES/REMEDIES FOR MUSCLE TISSUE DEGENERATIONS

[75] Inventors: Norifumi Nakamura; Mamoru Koyama, both of Hirakata; Mizuo Miyazaki, Nagaokakyo, all of Japan

[73] Assignees: Yoshitomi Pharmaceutical Industries, Ltd.; Asahi Glass Co., Ltd., both of Japan

[21] Appl. No.: 09/254,044

[22] PCT Filed: Aug. 27, 1997

[86] PCT No.: PCT/JP97/02992

§ 371 Date: May 10, 1999

§ 102(e) Date: May 10, 1999

[87] PCT Pub. No.: WO98/08514

PCT Pub. Date: Mar. 5, 1998

[30] Foreign Application Priority Data

Aug. 30, 1996 [JP] Japan ..................... 8-230936

[51] Int. Cl.⁷ .......... A61K 31/52; A61K 31/44; A61K 31/47
[52] U.S. Cl. .......... 514/262; 514/265; 514/266; 514/303; 514/312; 514/314; 514/907
[58] Field of Search .................. 514/262, 265, 514/266, 303, 312, 314, 907

[56] References Cited

U.S. PATENT DOCUMENTS

| | | | |
|---|---|---|---|
| 5,389,642 | 2/1995 | Dorsch et al. | 514/303 |
| 5,478,832 | 12/1995 | Inoue et al. | 514/266 |

FOREIGN PATENT DOCUMENTS

| | | |
|---|---|---|
| 0 574 846 | 12/1993 | European Pat. Off. . |
| 6-56832 | 3/1994 | Japan . |
| 6-92939 | 4/1994 | Japan . |

OTHER PUBLICATIONS

CA 125:33491, Ito et al., Mar. 1996.
*Patent Abstracts of Japan*, abstract of JP 6–80664. (1994).
*Patent Abstracts of Japan*, abstract of JP 8–73458. (1996).
*Patent Abstracts of Japan*, abstract of JP 6–92939. (1994).
Yamagishi et al., *J. Mol. Cell. Cardiol.*, 25, 1369–1380(1993).

*Primary Examiner*—Kimberly Jordan
*Attorney, Agent, or Firm*—Wenderoth, Lind & Ponack, L.L.P.

[57] ABSTRACT

An agent for the prophylaxis or treatment of muscle tissue degeneration, containing, as an active ingredient, a quinoline compound of the formula (I):

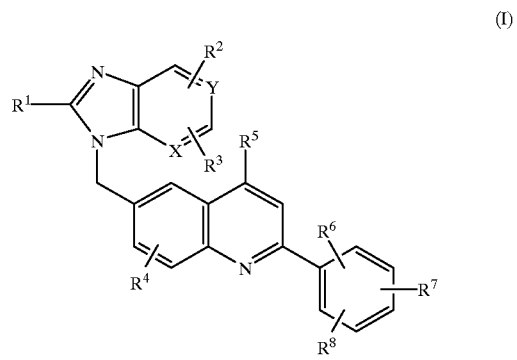

or a pharmaceutically acceptable salt. The prophylactic or therapeutic agent of muscle tissue degeneration of the present invention contains a quinoline compound of the formula (I) or a pharmaceutically acceptable salt thereof as an active ingredient, and shows remarkable inhibitory or improving action on degeneration of the muscle tissues such as necrosis, fibrosis, calcification and the like. The agent is specifically useful for the prophylaxis and treatment of cardiomyopathy, muscular dystrophy, pulmonary fibrosis and the like.

3 Claims, 1 Drawing Sheet

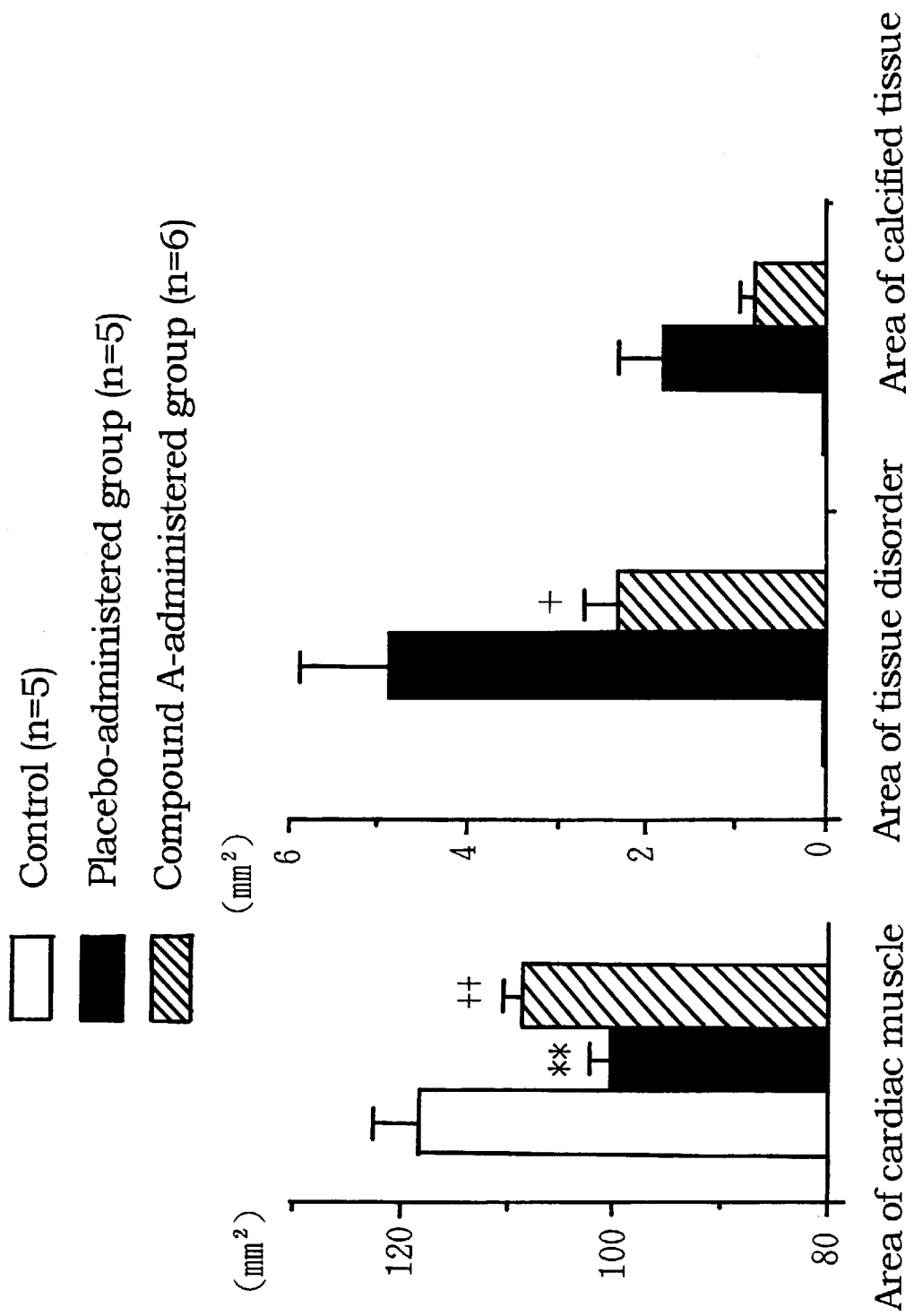

PREVENTIVES/REMEDIES FOR MUSCLE TISSUE DEGENERATIONS

This application is a PCT/JP97/02992, filed Aug. 27, 1997.

TECHNICAL FIELD

The present invention relates to an agent for the prophylaxis and treatment of muscle tissue degeneration, which contains a specific quinoline compound as an active ingredient.

BACKGROUND ART

In recent years, patients with diseases associated with muscle tissue degeneration, such as cardiomyopathy, muscular dystrophy, pulmonary fibrosis and the like, have been increasing in number, and greater attention has been paid to the prophylaxis and treatment of these diseases.

Cardiomyopathy is an idiopathic disease of cardiac muscle and is classified into dilated (congestive) cardiomyopathy, hypertrophic cardiomyopathy, restrictive cardiomyopathy and the like. The dilated cardiomyopathy is characterized by ventricular dilation and lower contraction function, wherein degeneration and atrophy of cardiac muscle of left ventricle or both ventricles and fibrosis of interstitium are observed. It shows the state of congestive heart failure, and is associated with grave convalescence. Hypertrophic cardiomyopathy accompanies nonuniform thickening of ventricle and irregular alignment of cardiac muscle cells (intricate alignment) mainly in the interventricular septum, and the convalescence varies from no symptom to heart failure, sudden death and the like. Restrictive cardiomyopathy mostly accompanies dilation disorder caused by endocardial or subendocardial fibrous hyperplasia, and is extremely intractable.

The treatment of cardiomyopathy includes administration of vasodilators (e.g., prazosin, hydralazine and the like), angiotensin conversion enzyme inhibitors (e.g., captopril and the like) and the like for symptomatic therapy of dilated cardiomyopathy. As a complete cure, heart transplantation is effective, but the operation is unfeasible in our country. To treat hypertrophic cardiomyopathy, β blockers (e.g., propranolol and the like) and Ca antagonists (e.g., verapamil, diltiazem and the like) have been used.

The above-mentioned treatments currently applied in our country, nevertheless, are all symptomatic therapies of various symptoms of cardiomyopathy, and are not complete cures that improve degeneration itself of the cardiac muscle. In other words, conventional treatment methods cannot positively suppress the progression of the disease conditions, and therefore, the criticality of heart failure, sudden death and the like associated with patients with cardiomyopathy cannot be reduced with ease.

In addition, there exists no effective medication of muscular dystrophy or pulmonary fibrosis.

On the other hand, angiotensin II antagonist, which is effective for the treatment of hypertension and the like, has been attracting much attention in recent years. The angiotensin II antagonist is a medication that prevents, at a receptor on the cell membrane, angiotensin II, that shows strong vasocontraction and acts on adrenal cortex to promote secretion of aldosterone, thereby causing higher blood pressure, from functioning via the receptor.

Nakamura et al. reported (Am. J. Physiol. Dec. 1994, 267, H2297–2304) that a representative angiotensin II antagonist, TCV-116, was investigated for the action on hamsters with cardiomyopathy, but the action of this drug, which was administered in a high dose, was only the improvement of heart function and that the drug failed to show a basic histological improvement.

Under the circumstances, there is a demand for the development of a medication that can inhibit or improve degeneration of muscle tissues, such as necrosis, fibrosis, calcification and the like, and that is capable of preventing or completely treating cardiomyopathy, muscular dystrophy, pulmonary fibrosis and the like by this action.

It is therefore an object of the present invention to provide a prophylactic and therapeutic agent of muscle tissue degeneration, which is capable of inhibiting or improving necrosis, fibrosis, calcification and the like of muscle tissues.

DISCLOSURE OF THE INVENTION

The present inventors have conducted various studies of a therapeutic method of cardiomyopathy and the like, in an attempt to achieve the above-mentioned problems, and found for the first time that a specific quinoline compound known to be useful as an angiotensin II antagonist for the treatment of hypertension and the like and a pharmaceutically acceptable salt thereof have superior actions of inhibition or improvement of degeneration of muscle tissues, such as necrosis, fibrosis, calcification and the like, which resulted in the completion of the present invention.

Accordingly, the present invention provides the following.

(1) An agent for the prophylaxis or treatment of muscle tissue degeneration, containing, as an active ingredient, a quinoline compound of the formula (I):

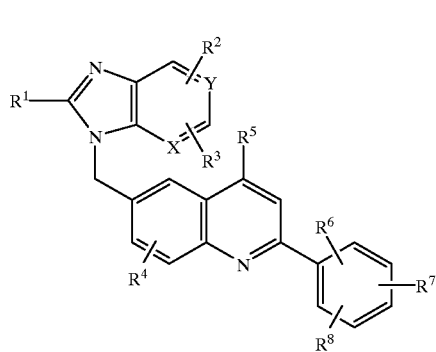

wherein, in the formula (I), $R^1$ to $R^8$ mean the following:

$R^1$: lower alkyl, halo(lower)alkyl, cyclo(lower)alkyl, alkenyl, alkoxyl, alkoxy(lower)alkyl or alkylthio, $R^2$, $R^3$: may be the same or different and each is independently hydrogen atom, halogen atom, lower alkyl, halo(lower)alkyl, cyclo(lower)alkyl, alkenyl, alkoxyl, $C_mF_{2m+1}$—, —$(CH_2)_nR^9$ or —$(CH_2)_pCOR^{10}$, $R^4$: hydrogen atom, halogen atom, lower alkyl, alkoxyl or $C_mF_{2m+1}$—, $R^5$: hydrogen atom, halogen atom, —COOH, -COOR$^{11}$, —CONH$_2$ or —CN, $R^6$: —COOH, —COOR$^{12}$, —CONH$_2$, —CN, —NHSO$_2$CF$_3$ or C-bound tetrazolyl, $R^7$, $R^8$: may be the same or different and each is independently hydrogen atom, halogen atom, lower alkyl, alkoxyl or $C_mF_{2m+1}$—, and X, Y: may be the same or different and each is independently CH or nitrogen atom, wherein, $R^9$–$R^{12}$, m, n and p above mean the following:

$R^9$: hydroxyl or alkoxyl, $R^{10}$: hydrogen atom, hydroxyl, lower alkyl or alkoxyl, $R^{11}$, $R^{12}$: may be the same or different and each is independently lower alkyl, alkenyl, cyclo(lower)alkyl, aryl or aralkyl, m: an integer of 1 to 6, n: an integer of 1 to 4, and p: an integer of 0 to 4, or a pharmaceutically acceptable salt thereof.

(2) The agent for the prophylaxis or treatment of muscle tissue degeneration of (1), wherein the quinoline compound of the formula (I) is N-{2-{6-[(2-ethyl-5,7-dimethyl-3H-imidazo[4,5-b]pyridin-3-yl)methyl]quinolin-2-yl}phenyl}trifluoromethanesulfonamide.

(3) The agent for the prophylaxis or treatment of muscle tissue degeneration of (1) or (2), which is at least one member selected from the group consisting of a prophylactic or therapeutic agent of cardiomyopathy, a prophylactic or therapeutic agent of muscular dystrophy, and a prophylactic or therapeutic agent of pulmonary fibrosis.

(4) A pharmaceutical composition for the prophylaxis or treatment of muscle tissue degeneration, containing a quinoline compound of the formula (I) or a pharmaceutically acceptable salt thereof, and a pharmaceutically acceptable carrier.

(5) The pharmaceutical composition for the prophylaxis or treatment of muscle tissue degeneration of (4), wherein the quinoline compound of the formula (I) is N-{2-{6-[(2-ethyl-5,7-dimethyl-3H-imidazo[4,5-b]pyridin-3-yl)methyl]quinolin-2-yl}phenyl}trifluoromethanesulfonamide.

(6) The pharmaceutical composition for the prophylaxis or treatment of muscle tissue degeneration of (4) or (5), wherein the muscle tissue degeneration is at least one member selected from the group consisting of cardiomyopathy, muscular dystrophy and pulmonary fibrosis.

(7) A method for the prophylaxis or treatment of muscle tissue degeneration, comprising administering an effective amount of the quinoline compound of the formula (I) or a pharmaceutically acceptable salt thereof to a patient.

(8) The method for the prophylaxis or treatment of muscle tissue degeneration of (7), wherein the quinoline compound of the formula (I) is N-{2-{6-[(2-ethyl-5,7-dimethyl-3H-imidazo[4,5-b]pyridin-3-yl)methyl]quinolin-2-yl}phenyl}trifluoromethanesulfonamide.

(9) The method of (7) or (8) for the prophylaxis or treatment of muscle tissue degeneration, wherein the muscle tissue degeneration is at least one member selected from the group consisting of cardiomyopathy, muscular dystrophy and pulmonary fibrosis.

(10) Use of the quinoline compound of the formula (I) or a pharmaceutically acceptable salt thereof for the production of a prophylactic or therapeutic drug for muscle tissue degeneration.

(11) The use of (10), wherein the quinoline compound of the formula (I) is N-{2-{6-[(2-ethyl-5,7-dimethyl-3H-imidazo[4,5-b]pyridin-3-yl)methyl]quinolin-2-yl}phenyl}trifluoromethanesulfonamide.

(12) The use of (10) or (11), wherein the muscle tissue degeneration is at least one member selected from the group consisting of cardiomyopathy, muscular dystrophy and pulmonary fibrosis.

(13) A commercial package comprising the pharmaceutical composition for the prophylaxis or treatment of muscle tissue degeneration of any of (4) to (6), and a written matter, the written matter stating that the pharmaceutical composition can be or should be used for the prophylaxis or treatment of muscle tissue degeneration.

The quinoline compound of the formula (I) and a pharmaceutically acceptable salt thereof to be used in the present invention are useful as an angiotensin II antagonist for the treatment of hypertension and the like, and are known to have characteristic features of low toxicity, superior absorption performance, stability and duration (Japanese Patent Unexamined Publication No. 6-80664).

The pharmaceutically acceptable salt of the quinoline compound of the formula (I) may be an acid addition salt derived from this quinoline compound and an inorganic acid or organic acid. Examples of such salt include hydrochloride, hydrobromide, sulfate, phosphate, methanesulfonate, p-toluenesulfonate, oxalate, tartarate, citrate, maleate, fumarate, succinate, lactate, glutalate, acetate, trifluoroacetate, salts with various amino acids and the like.

The pharmaceutically acceptable salt of the quinoline compound of the formula (I) may be a salt formed by this quinoline compound and a base. Examples of the salt include salts formed from alkali metal (e.g., sodium and potassium), alkaline earth metal (e.g., calcium and magnesium), ammonium and substituted ammonium (e.g., dimethyl ammonium and triethyl ammonium), and the like.

In the foregoing and subsequent explanation of the present invention, the "lower" organic group means that the group has 1 to 6 carbon atoms. The "lower alkyl" may be linear or branched and suitable examples thereof include methyl, ethyl, propyl, isopropyl, butyl, isobutyl, t-butyl, pentyl, hexyl and the like. The "halo(lower)alkyl" is a lower alkyl substituted by halogen, which is suitably exemplified by chloromethyl, 2-chloroethyl, bromomethyl, 2-bromoethyl, 1,2-dichloroethyl, 1,2-dibromoethyl, 3-trifluoromethylpropyl and the like. The "lower cycloalkyl" is a cycloalkyl wherein the number of carbon atoms constituting the ring is 3 to 6, which is suitably exemplified by cyclopropyl, cyclobutyl, cyclopentyl, cyclohexyl and the like.

The "alkenyl" is preferably lower alkenyl and more preferably linear or branched alkenyl having 2 to 4 carbon atoms, which is suitably exemplified by vinyl, allyl, 1-propenyl, isopropenyl, 1-butenyl and the like. The "alkoxyl" is preferably lower alkoxyl, and more preferably linear or branched alkoxyl having 1 to 4 carbon atoms, which is suitably exemplified by methoxy, ethoxy, propoxy, butoxy and the like. The "alkoxy(lower)alkyl" preferably has an alkoxyl moiety of lower alkoxyl. Suitable examples thereof include methoxyethyl, 3-methoxypropyl, 2-ethoxyethyl and the like. The "alkylthio" is preferably lower alkylthio, which is suitably exemplified by methylthio, ethylthio, propylthio, butylthio and the like.

In the foregoing and subsequent explanation of the present invention, the "halogen atom" means fluorine atom, chlorine atom, bromine atom and iodine atom. The "aryl" is a monovalent aromatic hydrocarbon which may have a substituent (e.g., lower alkyl, halogen atom, lower alkoxyl, lower alkylamino and the like). Preferred are phenyl and its derivatives such as phenyl, tolyl, p-halophenyl (e.g., p-chlorophenyl, p-bromophenyl and the like), alkoxyphenyl (e.g., methoxyphenyl, ethoxyphenyl and the like), dialkylaminophenyl (e.g., dimethylaminophenyl, diethylaminophenyl and the like), and the like. The "aralkyl" is aryl-substituted alkyl wherein the aryl as a substituent is those mentioned above and the number of carbon atom of alkyl is preferably 1 to 4. Suitable examples thereof include benzyl, benzhydryl, trityl, phenethyl and the like.

Of the quinoline compounds of the formula (I), preferred compound is that wherein $R^1$ is lower alkyl or alkenyl, $R^2$ and $R^3$ may be the same or different and each is independently hydrogen atom, halogen atom, lower alkyl, —$(CH_2)_n R^9$ or —$(CH_2)_p COR^{10}$ (wherein $R^9$ is hydroxyl or alkoxyl, $R^{10}$ is hydrogen atom, hydroxyl or alkoxyl, n is an integer of 1 to 4 and p is an integer of 0 to 4), $R^4$ is hydrogen atom, $R^5$ is hydrogen atom, —COOH or —$COOR^{11}$ (wherein $R^{11}$ is lower alkyl, alkenyl, cyclo(lower)alkyl, aryl or aralkyl), $R^6$ is —COOH, —$COOR^{12}$ (wherein $R^{12}$ is lower alkyl, alkenyl, cyclo(lower)alkyl, aryl or aralkyl), —$NHSO_2CF_3$ or C-bound tetrazolyl, $R^7$ and $R^8$ may be the same or different and each is independently hydrogen atom, fluorine atom, chlorine atom, lower alkyl or alkoxyl, X is nitrogen atom and Y is CH.

Of the quinoline compounds of the formula (I), more preferred compound is that wherein $R^1$ is lower alkyl, $R^2$ and $R^3$ may be the same or different and each is independently hydrogen atom, lower alkyl, —$(CH_2)_n R^9$ or —$(CH_2)_p COR^{10}$ (wherein $R^9$ is hydroxyl, $R^{10}$ is hydrogen atom, hydroxyl or alkoxyl, n is 1, p is 0–1), $R^4$ is hydrogen atom, $R^5$ is hydrogen atom or chlorine atom, $R^6$ is —COOH, —$COOR^{12}$ (wherein $R^{12}$ is lower alkyl, alkenyl, cyclo (lower)alkyl, aryl or aralkyl), —$NHSO_2CF_3$ or C-bound tetrazolyl, $R^7$ and $R^8$ may be the same or different and each is independently hydrogen atom, fluorine atom, chlorine atom or lower aLkyl, X is nitrogen atom and Y is CH.

The most preferable quinoline compound in terms of prophylaxis and treatment effect on muscle tissue degeneration is a compound of the following formula (II): N-{2-{6-[(2-ethyl-5,7-dimethyl-3H-imidazo[4,5-b]pyridin-3-yl)methyl]quinolin-2-yl}phenyl}trifluoromethanesulfonamide and a pharmaceutically acceptable salt thereof.

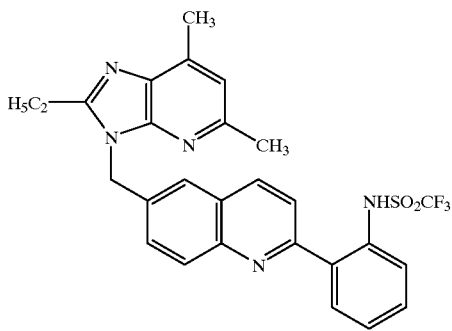

(II)

The quinoline compound of the formula (I) to be used in the present invention is a known compound and can be prepared by a method known in the art, such as the method disclosed in Japanese Patent Unexamined Publication No. 6-80664.

The prophylactic and therapeutic agent of muscle tissue degeneration of the present invention contains the quinoline compound of the formula (I) or a pharmaceutically acceptable salt thereof as an active ingredient, and shows a remarkable inhibitory and improving effects on the degeneration of muscle tissues (e.g., necrosis, fibrosis, calcification and the like) of mammals inclusive of human, monkey, dog, cat, horse, cow and the like. In addition, the compound (I) shows low toxicity, superior absorption performance, stability, duration and the like, and can be beneficially used specifically for the prophylaxis and treatment of cardiomyopathy, muscular dystrophy, pulmonary fibrosis and the like.

When the prophylactic and therapeutic agent of muscle tissue degeneration of the present invention is administered for the treatment or prophylaxis, the quinoline compound of the formula (I) or a pharmaceutically acceptable salt thereof as an active ingredient is formulated to have a dosage form suitable for oral administration, parenteral administration or external administration, using a pharmaceutically acceptable carrier and the like, into a solid preparation (e.g., tablet, granule, capsule, powder and the like), a liquid preparation (e.g., liquid, suspension, syrup, emulsion, lemonade and the like) and the like and used as a pharmaceutical preparation. Where necessary, a conventional additive, such as auxiliary agent, stabilizer, wetting agent and the like, which are exemplified by lactose, citric acid, tartaric acid, stearic acid, magnesium stearate, white clay, sucrose, corn starch, talc, gelatin, agar, pectin, peanut oil, olive oil, cacao oil, ethylene glycol and the like, may be added to the above-mentioned preparation.

An effective amount of the quinoline compound of the formula (I) or a pharmaceutically acceptable salt thereof is contained in the above-mentioned preparation. While the content thereof varies depending on the administration route, the kind of disease, conditions, body weight and age of patient, and the like, generally 0.01 mg to about 500 mg or above is administered daily to a patient. An average dose is about 0.05 mg, 0.1 mg, 0.25 mg, 0.5 mg, 1 mg, 20 mg, 50 mg, 100 mg, 200 mg or 300 mg for the prophylaxis and treatment of muscle tissue degeneration.

BRIEF DESCRIPTION OF THE DRAWING

FIG. 1 shows the area of cardiac muscle, area of tissue disorder and area of calcified tissue of control hamster, cardiomyopathic hamster administered with placebo and cardiomyopathic hamster administered with compound A, wherein each value is mean±standard error (n=5–6), **: P<0.01 (t-test against control), +: P<0.05, ++: P<0.01 (t-test against group administered with placebo).

EXAMPLES

The present invention is explained in detail in the following by way of Example and Experimental Examples, to which the present invention is not limited.

Reference Example

Production of N-{2-{6-[(2-ethyl-5,7-dimethyl-3H-imidazo[4,5-b]pyridin-3-yl)methyl]quinolin-2-yl}phenyl}trifluoromethanesulfonamide 2-{6-[(2-Ethyl-5,7-dimethyl-3H-imidazo[4,5-b]pyridin-3yl)methyl]quinolin-2-yl}aniline (8.73 g, 21.4 mmol) prepared by the method disclosed in Japanese Patent Unexamined Publication No. 6-80664, triethylamine (6.0 ml, 42.8 mmol) and chloroform (87 ml) were mixed and stirred. While cooling on an ice-bath, a solution of anhydrous trifluoromethanesulfonic acid (3.6 ml, 21.4 mmol) in chloroform (36 ml) was added dropwise over 50 minutes. After stirring for 10 minutes, 2M acetic acid (123 ml) was added dropwise under ice-cooling. The solution was partitioned and the organic layer was washed twice with ion exchange water (123 ml), once with 2% aqueous hydrogencarbonate solution (123 ml) and once with ion exchange water (123 ml) to give a crude solution of N-{2-{6-[(2-ethyl-5,7-dimethyl-3H-imidazo[4,5-b]pyridin-3-yl)methyl]quinolin-2-yl}phenyl}trifluoromethanesulfonamide in chloroform. To this solution was added ethanol (60 ml), and the mixture was heated to a bath temperature of 90–115° C. to distill away 176 ml thereof. After standing still overnight at 0° C., the precipitated crystals were collected by filtration. The crystals were washed 3 times with ethanol (10 ml) and dried under reduced pressure. Of the obtained crystals (8.48 g), 8.36 g was taken. Thereto were added ethyl acetate (425 ml) and ethanol (175 ml), and the mixture was heated to distill away 325 ml thereof. The reaction mixture was stood still at room temperature and the precipitated crystals were collected by filtration. After washing 3 times with ethanol (10 ml), the crystals were dried under reduced pressure to give 6.36 g of crystals. This recrystallization step was repeated to give 5.52 g of N-{2-{6-[(2-ethyl-5,7-dimethyl-3H-imidazo[4,5-b]pyridin-3-yl)methyl]quinolin-2-yl}phenyl}trifluoromethanesulfonamide as yellow crystals, melting point 252.0° C.

$^1$H-NMR (400 MHz, CDCl$_3$) δ (ppm): 8.22 (d, J=9.2 Hz, 1H); 7.99–8.05 (m, 3H); 7.84 (d, J=8.0 Hz, 1H); 7.69 (dd, J=8.6,1.4 Hz, 1H); 7.48 (t, J=7.2 Hz, 1H); 7.43 (s, 1H); 7.29 (t, J=8.0 Hz, 1H); 6.94 (s, 1H); 5.67 (s, 2H); 2.82 (q, J=7.6 Hz, 2H); 2.67 (s, 3H); 2.60 (s, 3H); 1.34 (t, J=7.6 Hz, 3H). $^{19}$F-NMR (400 MHz, CDCl$_3$) δ (ppm): −77.183

Experimental Examples

Test of cardiomyopathy inhibitory action

Cardiomyopathic hamsters (Bio 14.6:male, 4 weeks old) were divided into two groups, and N-{2-{6-[(2-ethyl-5,7-dimethyl-3H-imidazo[4,5-b]pyridin-3-yl)methyl]quinolin-2-yl}phenyl}trifluoromethanesulfonamide (3 mg/kg, hereinafter to be referred to as compound A) was orally administered to one group (6 hamsters) and placebo (3 mg/kg) to the other group (5 hamsters) once a day for 9 weeks. As the control hamsters, Bio FIB (male, 5 hamsters, 4 weeks old) were bred for 9 weeks under the same conditions as above. After 9 weeks, the following evaluation was performed.

1. Evaluation by histological analysis of heart

Method for preparation of sample

The animals were slaughtered and the heart was removed and immobilized with 10% neutral-buffered formalin. The heart was divided into 5 parts, and the slices of each part were embedded in paraffin, with the same plane facing up, to give samples of cardiomyopathy at 4 sites per one hamster.

The above-mentioned samples were subjected to Azan staining [Nihon Byori Gakkai Ed.: Byori Gijutsu Manual 3, Byori Soshiki Hyouhon Sakusei Gijutsu (last vol.) Senshokuhou 46–51, Ishiyaku Shuppan, 1981] and Ca staining [Nihon Byori Gakkai Ed.: Byori Gijutsu Manual 3, Byori Soshild Hyouhon Sakusei Gijutsu (last vol.) Senshokuhou 143–147, Ishiyaku Shuppan, 1981] and the total area, area of tissue disorder and calcified area of cardiac muscle were measured using an image analyzer (LUZEX-F, manufactured by NIRECO Co. Ltd.).

Evaluation method 1

All samples of the groups administered with compound A and placebo (former: 24 samples, latter: 20 samples) were evaluated for the area of tissue disorder and the calcified area based on the average area. The results are shown in Tables 1 and 2.

TABLE 1

Area of tissue disorder (mm$^2$)

| | |
|---|---|
| Compound A-administered group (n = 24) | 0.58 ± 0.1 |
| Placebo-administered group (n = 20) | 1.22 ± 0.2 | p < 0.01

TABLE 2

Calcified area (mm$^2$)

| | |
|---|---|
| Compound A-administered group (n = 24) | 0.19 ± 0.01 |
| Placebo-administered group (n = 20) | 0.45 ± 0.09 | p < 0.01

Evaluation method 2

Taking the total area of the 4 samples obtained from each hamster as the area of the hamster, the groups administered with compound A and placebo and control were evaluated for the area of cardiac muscle, the area of tissue disorder and the area of calcified tissue based on the average area of all hamsters. The results are shown in FIG. 1.

Results

The heart of the cardiomyopathic hamsters (placebo-administered group) showed noticeable atrophy of cardiac muscle, and necrosis, fibrosis and calcification of the cardiac muscle were acknowledged. The group administered with compound A showed significant inhibition of atrophy of the cardiac muscle and the area of disorder. It was clarified that the administration of compound A markedly improved pathological tissue change of the heart of the cardiomyopathic hamsters.

2. Other evaluations

A biochemical analysis of serum revealed striking increase in serum LDH, GOT, GPT and CPK values of the cardiomyopathic hamsters. The administration of compound A resulted in an appreciable inhibition of the increase thereof. In addition, the administration of compound A did not cause significant changes in the body weight, heart weight and blood pressure.

Formulation Examples are given in the following.

Formulation Example 1

Tablets

| | | |
|---|---|---|
| 1) Compound A | | 10.0 mg |
| 2) Fine particles No. 209 for direct compression (manufactured by Fuji Chemical) | | 46.6 mg |
| Sodium alumina metasilicate | 20 wt % | |
| Corn starch | 30 wt % | |
| Lactose | 50 wt % | |
| 3) Crystalline cellulose | | 24.0 mg |
| 4) Calcium carboxylmethylcellulose | | 4.0 mg |
| 5) Magnesium stearate | | 0.4 mg |

3), 4) and 2) were respectively dried to a certain water content and mixed at the above-mentioned weight ratios in a mixer. To the homogeneous mixture was added 5) and they were mixed for a short time (30 seconds). The mixture was compressed (pounder 6.3 mmΦ, 6.0 mmR) to give tablets of 8.5 mg per tablet.

This tablet may be coated with a conventional enteric film [e.g., poly(vinyl acetal)diethylaminoacetate] or edible coloring where necessary.

Formulation Example 2

Capsules

| | |
|---|---|
| 1) Compound A | 50 g |
| 2) Lactose | 935 g |
| 3) Magnesium stearate | 15 g |

The above ingredients were weighed and homogeneously mixed. The mixed powder was packed in hard gelatin capsules by 200 mg each.

| Formulation Example 3 | |
| --- | --- |
| Injections | |
| 1) Compound A | 5 mg |
| 2) Sucrose | 100 mg |
| 3) Physiological saline | 10 ml |

A mixed solution of the above ingredients was filtered through a membrane filter and sterilized by filtration again. The filtrate was aseptically dispensed to vials and, after filling a nitrogen gas, sealed to give intravenous injection.

INDUSTRIAL APPLICABILITY

The prophylactic and therapeutic agent of muscle tissue degeneration of the present invention shows superior improving action on tissue lesion of the muscle tissues, such as necrosis, fibrosis, calcification and the like, and has low toxicity. Therefore, the agent is specifically useful for the prophylaxis and treatment of cardiomyopathy, muscular dystrophy, pulmonary fibrosis and the like.

This application is based on application No. 230936/1996 filed in Japan, the content of which is incorporated hereinto by reference.

What is claimed is:

1. A method for the prophylaxis or treatment of muscle tissue degeneration, comprising administering to a patient in need of same an effective amount of the quinoline compound of the formula (I):

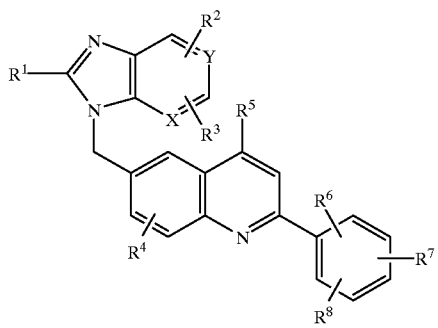

(I)

wherein, in the formula (I), $R^1$ to $R^8$ mean the following:

$R^1$: lower alkyl, halo(lower)alkyl, cyclo(lower)alkyl, alkenyl, alkoxyl, alkoxy(lower)alkyl or alkylthio, $R^2$, $R^3$: may be the same or different and each is independently hydrogen atom, halogen atom, lower alkyl, halo(lower)alkyl, cyclo(lower)alkyl, alkenyl, alkoxyl, $C_mF_{2m+1}$—, —$(CH_2)_nR^9$ or —$(CH_2)_pCOR^{10}$, $R^4$: hydrogen atom, halogen atom, lower alkyl, alkoxyl or $C_mF_{2m+1}$—, $R^5$: hydrogen atom, halogen atom, —COOH, -COOR$^{11}$, —CONH$_2$ or —CN, $R^6$: —COOH, —COOR$^{12}$, —CONH$_2$, —CN, —NHSO$_2$CF$_3$ or C-bound tetrazolyl, $R^7$, $R^8$: may be the same or different and each is independently hydrogen atom, halogen atom, lower alkyl, alkoxyl or $C_mF_{2m+1}$—, and X, Y: may be the same or different and each is independently CH or nitrogen atom, wherein, $R^9$–$R^{12}$, m, n and p above mean the following:

$R^9$: hydroxyl or alkoxyl, $R^{10}$: hydrogen atom, hydroxyl, lower alkyl or alkoxyl, $R^{11}$, $R^{12}$: may be the same or different and each is independently lower alkyl, alkenyl, cyclo(lower)alkyl, aryl or aralkyl, m: an integer of 1 to 6, n: an integer of 1 to 4, and p: an integer of 0 to 4, or a pharmaceutically acceptable salt thereof, to a patient.

2. The method for the prophylaxis or treatment of muscle tissue degeneration of claim 1, wherein the quinoline compound of the formula (I) is N-{2-{6-[(2-ethyl-5,7-dimethyl-3H-imidazo[4,5-b]pyridin-3-yl)methyl]quinolin-2-yl}phenyl}trifluoromethanesulfonamide.

3. The method of claim 1 or claim 2 for the prophylaxis or treatment of muscle tissue degeneration, wherein the muscle tissue degeneration is at least one member selected from the group consisting of cardiomyopathy, muscular dystrophy and pulmonary fibrosis.

* * * * *